United States Patent [19]

Weissbach et al.

[11] Patent Number: 5,562,733
[45] Date of Patent: Oct. 8, 1996

[54] DENTAL CERAMIC, COATED TITANIUM PROSTHESIS

[75] Inventors: Klaus Weissbach, Bad Kreuznach; Klaus Krumbholz, Langen; Ralf Janda, Karben, all of Germany

[73] Assignee: Dentsply G.m.b.H., Dreieich, Germany

[21] Appl. No.: 219,755

[22] Filed: Mar. 29, 1994

Related U.S. Application Data

[63] Continuation of Ser. No. 872,228, Apr. 22, 1992, abandoned, which is a continuation-in-part of Ser. No. 557,260, Jul. 24, 1990, abandoned.

[51] Int. Cl.⁶ ................................................. A61F 2/28
[52] U.S. Cl. .................. 623/16; 623/11; 433/201.1; 433/212.1; 433/222.1; 523/115
[58] Field of Search ............................ 433/201.1, 212.1, 433/222.1, 228.1; 623/11, 16, 66; 523/115, 116

[56] References Cited

U.S. PATENT DOCUMENTS

| | | | |
|---|---|---|---|
| 2,980,998 | 4/1961 | Colman et al. | 32/12 |
| 3,844,801 | 10/1974 | Wolf | 106/50 |
| 4,004,935 | 1/1977 | Grosvenor et al. | 106/48 |
| 4,159,358 | 6/1979 | Hench et al. | 427/318 |
| 4,198,244 | 4/1980 | Binns et al. | 106/35 |
| 4,215,033 | 1/1980 | Bowen | 260/42.15 |
| 4,361,654 | 11/1982 | Ohmura et al. | 501/21 |
| 4,431,451 | 2/1984 | Mabie et al. | 106/35 |
| 4,557,691 | 12/1985 | Martin et al. | 433/199.1 |
| 4,798,536 | 1/1989 | Katz | 433/212.1 |
| 4,814,298 | 3/1989 | Nelson et al. | 501/17 |
| 5,176,747 | 1/1993 | Panzera et al. | 433/212.1 |
| 5,308,391 | 5/1994 | Komma et al. | 433/212.1 |
| 5,314,334 | 5/1994 | Panzera et al. | 433/222.1 |
| 5,346,866 | 9/1994 | Komma et al. | 433/201.1 |

FOREIGN PATENT DOCUMENTS

| | | |
|---|---|---|
| 1081506 | 7/1980 | Canada. |
| 1120960 | 3/1982 | Canada. |
| 1129688 | 8/1982 | Canada. |
| 1146782 | 5/1983 | Canada. |
| 1156679 | 11/1983 | Canada. |
| 1177604 | 11/1984 | Canada. |
| 1193619 | 9/1985 | Canada. |
| 0119063 | 9/1984 | European Pat. Off.. |
| 0328772 | 8/1989 | European Pat. Off.. |
| 0332887 | 9/1989 | European Pat. Off.. |
| 2305169 | 10/1976 | France. |
| 2391175 | 12/1978 | France. |
| 2815438 | 10/1979 | Germany. |
| 2080281 | 2/1982 | United Kingdom. |

OTHER PUBLICATIONS

Medical Progress through Technology, vol. 9: 129–139(1982) de Groot.
J. Dent. Res., vol. 69(6): 1230–1235(1990) Adachi et al.

*Primary Examiner*—Paul B. Prebilic
*Attorney, Agent, or Firm*—Dale R. Lovercheck; James B. Bieber

[57] ABSTRACT

A bonding dental ceramic material and method of use thereof is provided. The bonding dental ceramic material includes at least one network former and between about 8 and 17 percent by weight $B_2O_3$. The bonding dental ceramic material does not contain more than 5% by weight of opacifier and/or pigment, and is adapted to bond to titanium or titanium alloy with a bond strength of at least 20 MPa. Preferably the bonding dental ceramic material has a melting point less than 800° C. and includes a fluxing agent. This bonding dental ceramic material is used to make dental crowns and bridges. The bonding dental ceramic material is applied to titanium or titanium alloy and fired at less than 800° C. Then an opaque dental ceramic material including at least one network former and more than 5% by weight of opacifier and/or pigment but less than 5% by weight $B_2O_3$ is applied to the bonding dental ceramic material and fired at less than 800° C. Preferably the bonding dental ceramic material has a melting temperature of less than 830° C., and does not have more than 5% by weight pigments and/or opacifiers, or more than 0.5% by weight fluoride.

14 Claims, No Drawings

DENTAL CERAMIC, COATED TITANIUM PROSTHESIS

This is a continuation of application Ser. No. 07/872,228, filed Apr. 22, 1992, now abandoned, which is a continuation-in-part of application Ser. No. 07/557,260 filed Jul. 24, 1990, now abandoned.

BACKGROUND OF THE INVENTION

This invention relates to a dental ceramic material and a dental prosthesis. In particular the invention provides a dental ceramic bonder and method of use thereof to form dental prostheses made of titanium or titanium alloys including crowns and bridges. In accordance with the invention dental prostheses are provided which have a strong and permanent bond formed between a bonding dental ceramic coating and a titanium or titanium alloy base.

Mabie et al., U.S. Pat. No. 4,431,451, disclose dental material. Binnes et al., U.S. Pat. No. 4,198,244, disclose fluorescing agents for dental porcelain. Fujui in U.K. Patent GB 2080281 B, discloses biologically active glass and/or glass ceramic compositions and implants coated therewith. Muterthies in European Patent Application 0332887 A2 discloses a process for the manufacture of metal-ceramic dental restorations and color systems. Wuesthoff et al in German Patent Application 2815438 disclose dental porcelain compositions. Yves in Canadian Patent 1177604 discloses metallic prosthesis coated with a vitreous enamel and a method for producing prosthesis dental enamels for nickel and chromium. Mabie et al, Binns et al, Fujui, Muterthies, Wuesthoff et al and Yves do not disclose dental porcelain compositions which have the benefits of the present invention. The compositions therein disclose have coefficients of thermal expansion greater than that of natural tooth material, firing temperatures (melting points) in the range of 900° to 950° C. (which is substantially higher than the maximum firing temperatures for dental ceramic materials coated on titanium), and/or fluoride (which causes corrosion of titanium). These compositions are not adapted to bond to titanium or titanium alloy with a bond strength of at least 20 MPa.

Martin et al in U. S. Pat. No. 4,557,691 disclose a dental porcelain paste and method of using the same. Bowen in U. S. Pat. No. 4,215,033 discloses a composite dental material.

The prior art does not disclose dental ceramic material adapted to bond to titanium or titanium alloy with a bond strength of at least 20 MPa.

It is an object of the present invention to provide a dental ceramic bonding material useful to form dental prostheses having a dental ceramic coating with a bond strength of at least 20 MPa when bonded to a titanium or titanium alloy base.

Throughout this disclosure, the term dental ceramic is defined as meaning any ceramic having a glassy and/or crystalline phase. Pigments as used throughout this disclosure refers to metal oxides which substantially reflect a narrow band of visible light, absorb at least a substantial portion of the remainder of the visible light spectrum and are less than 5% transparent to the broad spectrum of visible light. Opacifiers as used throughout this disclosure refers to metal oxides which reflect at least a substantial portion of a broad spectrum of visible light, and are less than 5% transparent to the broad spectrum of visible light. Clear ceramic material as used throughout this disclosure refers to metal oxides which are fused to a glassy state and which are more than 90% transparent to a broad spectrum of visible light. Network formers as used throughout this disclosure refers to metal oxides such as $SiO_2$ and $Al_1O_3$ which primarily function to strengthen a dental ceramic by network forming. However, as used herein network former does not refer to $B_2O_3$. Fluxing metal oxides, also called network modifiers, as used throughout this disclosure refers to metal oxides, such as $Li_2O$, $Na_2O$, $K_2O$, CaO, MgO and BaO, which interrupt strengthening metal oxide networks and effectively reduce the melting temperature of the dental ceramic.

SUMMARY OF THE INVENTION

A dental ceramic coating system is provided to coat crowns and bridges having a base made of titanium or titanium alloys in several tooth shades. The first component of the system applied to the base is a clear bonding dental ceramic material which contains between 8 and 17 weight-percent of boron oxide expressed as $B_2O_3$. This proportion of $B_2O_3$ is directly responsible for high bonding strength of the dental ceramic coating system to the titanium.

To make a dental prosthesis in accordance with the invention the bonding dental ceramic material is applied to the titanium or titanium alloy base and fired. Next opaque pigmented ceramic is applied to the fired bonding dental ceramic and then fired. This opaque pigmented ceramic covers the grey color of the titanium or titanium alloy. Next a dentin shaded ceramic is applied to the fired opaque pigmented ceramic and then fired. Finally an enamel shaded ceramic is applied to the fired dentin shaded ceramic and then fired.

Bonding dental ceramic material in accordance with the invention has the ability to optimally wet a titanium surface and to dissolve oxides which are formed on the titanium surface during the casting process. Thus, the bonding dental ceramic material is able to bond directly to the titanium surface and has a bond strength of at least 20 MPa. Adding more than 5% by weight of pigments or opacifiers to the bonding dental ceramic causes a reduction of this bonding strength. The dental ceramic materials, including opacifying, dentin and enamel dental ceramic materials, which are applied to the bonding dental ceramic do not require between 8 and 17 percent by weight $B_2O_3$. Thus, in accordance with the invention a bonding dental ceramic material and method of use thereof is provided. Bonding dental ceramic material in accordance with the invention includes at least one strengthening metal oxide and between about 8 and 17 percent by weight $B_2O_3$. The bonding dental ceramic material in accordance with the invention does not contain more than 5% by weight of opacifiers and/or pigments and is adapted to bond to titanium or titanium alloy with a bond strength of at least 20 MPa. This bonding dental ceramic material is used to make dental crowns and bridges. An opacifying dental ceramic material including at least one network former and more than 5% by weight of opacifiers and/or pigments is applied to the bonding dental ceramic material and fired at less than 800° C. Dentin, enamel and stain dental ceramic materials are sequentially applied and fired to obtain a desired tooth shade.

DESCRIPTION OF THE PREFERRED EMBODIMENTS

Veneering or overlaying of titanium or titanium alloy bases of dental prostheses (e.g. crowns, bridge frames, or prostheses parts) with ceramic material is provided in accordance with the invention. Dental prostheses are preferably made of titanium or titanium alloys because of their biocompatibility with the soft and hard tissues of the oral cavity and the development of new casting methods and techniques. For example, titanium and titanium alloys are used in melting and casting procedures in a vacuum, in melting and casting procedures under an inert atmosphere, in computer assisted milling procedures and with spark erosion techniques. Titanium and its alloys have low density (specific weight), good erosion resistance and low price compared to precious or semi-precious metals.

The firing temperature for dental ceramics or titanium or titanium alloy should not exceed 880° C. Above this temperature or even above 830° C., titanium shows a significantly increased oxygen and nitrogen absorption as well as an alpha to beta structural modification. This increased absorption and structural modification lead to the embrittlement of the titanium surface where a decline in the strength takes place.

The thermal expansion of the bonding dental ceramic coating in accordance with the invention closely approximates the thermal expansion of titanium. The desired range for the coefficient of thermal expansion of the ceramic to be fused to the titanium is between $7.8 \times 10^{-6}/K$ to $9.0 \times 10^{-6}/K$ (25°–500° C.). Additionally, the bonding dental ceramic in accordance with the invention wets the titanium surface so that a ceramic-titanium bond is achieved. A bonding strength of at least 20 Megapascals (MPa), more preferably from about 22 to about 33 MPa, between titanium and titanium alloy and the bonding dental ceramic coating is attained so that prostheses in accordance with the invention are usable in the oral cavity for many years. Prior art dental ceramics with titanium show bonding strengths around 15 MPa (see Table I below).

Titanium and titanium alloy form a titanium oxide coating which does not permit the formation of direct bonding between a dental ceramic and the titanium or titanium alloy having a bond strength of at least 20 MPa. An unexpectedly superior feature of the invention is the formation of bonding between a dental ceramic and titanium or titanium alloy of at least 20 MPa. It is believed that from about 8 to about 17 percent by weight $B_2O_3$ in a bonding dental ceramic without more than 5% by weight pigments and/or opacifiers effectively removes the titanium oxide coating allowing the bonding dental ceramic to bond directly to the titanium or titanium alloy with a bond strength of at least 20 MPa.

To provide the esthetic requirements of dental ceramics titanium or titanium alloys are preferably veneered with multi-layers and/or multishades of dental ceramics in order to achieve natural appearing tooth colors and stains. The dental ceramics are obtained by producing at first a clear ceramic frit powder according to the following process: All raw material components are blended, fused together at temperatures above 1300° C., quenched in water, dried, and milled in order to form a clear ceramic frit powder. Opacifier, dentin, enamel and stain dental ceramics are formed by mixing the frit powder with suitable pigments, e.g. (Ti, Cr, Sb)$O_2$, (Ti, cr, w)$O_2$, (zn, cr, Fe, Al)$_xO_y$, (Zn, Cr, Fe, Al, Sn)$_xO_y$, (Zr, Si, Pr)$_xO_y$, (Sn, Sb, V)$_xO_y$, and opacifiers, e.g. $TiO_2$, $SnO_2$, $ZrSiO_4$, $ZrO_2$, in order to imitate the natural tooth shades.

A preferred embodiment of the invention provides a dental prosthesis including a bonding dental ceramic coating having between 8 and 17 weight-percent $B_2O_3$ that can be fused to titanium or titanium alloy base with a bonding strength of at least 20 MPa. The $B_2O_3$ in the bonding ceramic coating is directly responsible for the high bonding strength attained.

The bonding, opacifier, dentin, enamel and stain dental ceramics can be prepared as a dental ceramic powder or as a slurry suspension or paste in suitable organic and/or inorganic liquids. Such dental ceramic powder is preferably mixed with water to form an easily applied slurry. Alternatively, the dental ceramic powder is mixed with an organic material to form a mixture which is readily applied to the titanium or titanium alloy. Suitable organic material include methacrylate monomers. In an embodiment of the invention the slurry, suspension or paste contains polymerizable compounds (monomers or prepolymers) which are self-cured or cured by visible light and completely burned out of the dental ceramic coating when fired.

In accordance with the invention a prostheses is formed by mixing the dental ceramic powder with an aqueous vehicle to provide a slurry, supplying the slurry to a titanium or titanium alloy substrate to build-up the desired shape and thickness, and firing. Alternatively a dental prostheses in accordance with the invention are formed from dental ceramic powder, mixed with a curable resin modeling liquid vehicle to prepare a suspension or spreadable paste. The paste is applied to a dental restorative base made of titanium or titanium alloy to provide a coating of ceramic material thereon. The resin is then cured to effectively fix the coating of ceramic material in its desired shape and thickness. The coated dental restorative is then fired to fuse the ceramic material to the base. A method of preparation of a curable resin modeling liquid and the use of the liquid with a dental appliance are presented in U.S. Pat. No. 4,892,478 the contents of which are incorporated herein by reference.

The polymerizable resin modeling liquid used may be a one-component or multi-component light curable resin or a self-cured (chemically-cured) multi-component resin. In the firing step, the dental restorative is fired at temperatures effective to vaporize the volatile components of the resin without burning, charring or boiling and then to fuse the ceramic material. Typically, dental ceramic material in accordance with the invention has a melting (firing) temperature between 730° C. and 830° C. Preferably dental ceramic material in accordance with the invention has a melting temperature less than 830° C. More preferably dental ceramic material in accordance with the invention has a melting temperature less than 800° C.

Preferably dental ceramic material in accordance with the invention has less than 0.5% by weight fluoride. More preferably dental ceramic material in accordance with the invention has less than 0.1% by weight fluoride. Typically, dental ceramic material in accordance with the invention does not have any significant amount of fluoride, as fluoride causes corrosion of titanium and titanium alloy.

Preferably the bonding dental ceramic material in accordance with the invention has a melting (firing) temperature of less than 830° C., and does not have more than 5% by weight pigments and/or opacifiers, or more than 0.5% by weight fluoride. Preferably the bonding dental ceramic material in accordance with the invention has a melting point less than 800° C. and includes a fluxing agent.

Preferably bonding dental ceramic material in accordance with the invention is applied to a base made of titanium or titanium alloys and fired at less than 800° C.

A preferred embodiment of the present invention is disclosed in a bonding dental ceramic of the following composition:

| COMPOUND | WEIGHT-PERCENT |
|---|---|
| $SiO_2$ | 54–64, |
| $Al_2O_3$ | 5–12, |
| $B_2O_3$ | 8–17, |
| $Li_2O$ | 0.01–6, |
| $Na_2O$ | 3–10, |
| $K_2O$ | 0.01–8, |
| MgO | 0.01–2, |
| CaO | 0.01–6 and |
| BaO | 0.01–2. |

Other components, for example, opacifiers, pigments, other elements and/or impurities, may also be present in an amount of less than 5% by weight of the bonding dental ceramic.

A more preferred embodiment of a bonding dental ceramic in accordance with the invention has the following composition:

| COMPOUND | WEIGHT-PERCENT |
|---|---|
| $SiO_2$ | 58–64, |
| $Al_2O_3$ | 6–12, |
| $B_2O_3$ | 10–13, |
| $Li_2O$ | 2–5, |
| $Na_2O$ | 4–7, |
| $K_2O$ | 4–8 and |
| CaO | 3–5. |

The bonding dental ceramic composition is especially suited for a high bonding strength with titanium. The thermal expansion of titanium is a little higher than that of this bonding dental ceramic. The preferred firing temperature of bonding dental ceramic applied to titanium or titanium alloy is preferably between 740° and 830° C., more preferably between 770° and 800° C., and most preferably at 790° C.

Opacifier, dentin, enamel and stain dental ceramics are formed by mixing clear ceramic powder with suitable pigments e.g. $(Ti, Cr, Sb)O_2$, $(Ti, Cr, W)O_2$, $(Zn, Cr, Fe, Al)_xO_y$, $(Zn, Cr, Fe, Al, Sn)_xO_y$, $(Zr, Si, Pr)_xO_y$, $(Sn, Sb, V)_xO_y$, and opacifiers, e.g., $TiO_2$, $SnO_2$, $ZrO2$, $ZrSiO_4$, in order to imitate natural tooth shades. In this regard, a preferred embodiment of the dental ceramic containing pigments and opacifiers is the following composition:

| COMPOUND | WEIGHT-PERCENT |
|---|---|
| $SiO_2$ | 62–26, |
| $Al_2O_3$ | 5–12, |
| $B_2O_3$ | 0–5, |
| $Li_2O$ | 0–6, |
| $Na_2O$ | 3–10, |
| $K_2O$ | 0–8, |
| MgO | 0–2, |
| CaO | 0–6, |
| BaO | 0–2, |
| $TiO_2$ | 0–10, |
| $SnO_2$ | 0–10, |
| $ZrO_2$ | 0–10 and |
| Pigments | 0–10. |

This invention is further illustrated by the following Examples and Table:

EXAMPLE 1

A bonding dental ceramic was prepared by mixing the following raw materials in a share mixer:

| RAW MATERIAL | SUPPLIER | WEIGHT-PERCENT |
|---|---|---|
| Feldspar[1] | Dentsply International, York, PA | 29 |
| Quartz Flour | Bremthaler Quarzwerke, Usingen | 35 |
| $KNO_3$ | Riedel-de Haen, Seelze (Art. No. 12651) | 6 |
| $Na_2CO_3$ | Emesco, Frankfurt | 5 |
| $Li_2CO_3$ | Merck, Darmstadt, (Art. No. 5670) | 6 |
| $CaCO_3$ | Schäfer Kreice | 6 |
| $Na_2B_4O_7.10H_2O$ | Brenntag AG, Mühlheim/Ruhr | 6 |
| $B_2O_3$ | Riedel-de Haen, Seelze (Art. No. 31145) | 7 |

[1]dental grade potash feldspar as described in U.S. Pat. No. 4,604,366, the contents of which are incorporated herein by reference.

After mixing, the blend was continuously fused in a furnace at 1450° C. for 20 minutes. The resulting glassy melt was chilled in water, dried and ground in a ball mill until 50% of the grain size was 20 microns or less. The resulting bonding dental ceramic powder had the following composition:

| COMPOUND | WEIGHT-PERCENT |
|---|---|
| $SiO_2$ | 63.3 |
| $Al_2O_3$ | 6.4 |
| $B_2O_3$ | 10.8 |
| $Li_2O$ | 2.8 |
| $Na_2O$ | 5.7 |
| $K_2O$ | 7.0 |
| CaO | 4.0 |

The bonding dental ceramic powder was then mixed with water to provide a ceramic slurry. The slurry was applied to a dental substrate with a brush and the substrate and slurry fired in a furnace at 790° C. for 3 minutes. Of the 3 minutes in the furnace, 2.6 minutes were under vacuum ($\leq 50$ mbar).

EXAMPLE 2

A bonding dental ceramic was prepared as in Example 1 by mixing the following raw materials:

| RAW MATERIAL | SUPPLIER | WEIGHT-PERCENT |
|---|---|---|
| Feldspar K 31 | Mandt, GmbH & Co. KG, Brake | 51.0 |
| Quartz Flour | Bremthaler Quarzwerke, Usingen | 20.0 |
| $K_2CO_3$ | Merck, Darmstadt (Art. No. 4924) | 7.3 |
| $Li_2CO_3$ | Merck, Darmstadt (Art. No. 5670) | 4.4 |
| $CaCO_3$ | Merck, Darmstadt (Art. No. 2069) | 6.3 |
| $B_2O_3$ | Riedel-de Haen, Seelze (Art. No. 31145) | 11.0 |

Mixing, fusing, milling in water, drying, and grinding is carried out as in Example 1.

The resulting bonding dental ceramic powder had the following composition:

| COMPOUND | WEIGHT-PERCENT |
|---|---|
| $SiO_2$ | 60.4 |
| $Al_2O_3$ | 10.2 |
| $B_2O_3$ | 11.9 |
| $Li_2O$ | 1.9 |
| $Na_2O$ | 5.8 |
| $K_2O$ | 5.8 |
| CaO | 4.0 |

The bonding dental ceramic was subjected to a firing temperature of 800° C. and found to have a coefficient of thermal expansion of $8.0 \times 10^{-6}/K$ (25°–500° C.) and a resultant bond strength of 24 ±2 MPa. The bond strength was determined according to the Schmitz/Schulmeyer method (K. H. Schmitz and H. Schul meyer, Determination of bonding strength of dental—metal ceramic bonding systems, Dental-Labor, 23: 1416–1420, 1975).

EXAMPLE 3

A bonding dental ceramic containing an opacifier was prepared as in Example 1 by mixing the following raw materials:

| RAW MATERIAL | SUPPLIER | WEIGHT-PERCENT |
|---|---|---|
| Feldspar | Dentsply International, York, PA | 47.0 |
| Quartz Flour | Bremthaler Quarzwerke, Usingen | 22.0 |
| $Na_2CO_3$ | Emesco, Frankfurt | 4.0 |
| $Li_2CO_3$ | Merck, Darmstadt (Art. No. 5670) | 7.0 |
| $CaCO_3$ | Merck, Darmstadt (Art. No. 2069) | 6.0 |
| $TiO_2$, RN56 | Kronos Titan GmbH, Leverkusen | 2.0 |
| $B_2O_3$ | Riedel-de Haen, Seelze (Art. No. 31145) | 6.0 |
| $Na_2B_4O_7.10H_2O$ | Brenntag AG, Mühlheim/Rohr | 6.0 |

Mixing, fusing, milling in water, drying, and grinding is carried out as in Example 1.

The resulting bonding dental ceramic containing an opacifier had the following composition:

| COMPOUND | WEIGHT-PERCENT |
|---|---|
| $SiO_2$ | 60.0 |
| $Al_2O_3$ | 10.0 |
| $B_2O_3$ | 9.3 |
| $TiO_2$ | 2.3 |
| $Li_2O$ | 3.2 |
| $Na_2O$ | 5.5 |
| $K_2O$ | 5.9 |
| CaO | 3.9 |

Again, the bonding dental ceramic was subjected to a firing temperature of 800° C. and found to have a coefficient of thermal expansion of $8.0 \times 10^{-6}/K$ (25°–500° C.). As in Example 2, the resultant bond strength was determined according to the Schmitz/ Schulmeyer method to be 24 ±2 MPa.

Additional determinations of bonding strength between pure titanium and ceramic materials were performed and the results presented in Table I. Products I–IV are bonding dental ceramic materials of varying $B_2O_3$ content. DUCERATIN and TITANBOND are commercially available ceramics for bonding to titanium. DUCERATIN is the product of Ducera Dental GmbH, Rodheimer Str. 7, D-6365 Rosbach v.d.H., West Germany and TITANBOND is the product of Asami Tanaka Dental Enterprises Europe GmbH, Kaiser-Friedrich-Promenade 26, D-6380 Bad Homburg, v.d.H., West Germany. The bonding strength was determined according to the Schmitz/Schulmeyer method.

With more particular reference o table I products II and III are preferred embodiments of the invention. Product II is the product of Example 2. Products I and IV which are respectively below and above the preferred $B_2O_3$ content demonstrate lower bonding strength than products II and III.

TABLE I

| Product | Ti | I | II | III | IV | DUCERATIN | TITANBOND |
|---|---|---|---|---|---|---|---|
| Bonding Strength [MPa] | — | 14 ± 2 | 24 ± 2 | 20 ± 2 | 17 ± 2 | 15 ± 2 | 12 ± 2 |
| Thermal Expansion [$10^{-6}/K$.] | 9.3 | 8.7 | 8.0 | 8.2 | 8.6 | — | — |
| Firing Temperature [°C.] | — | 790 | 800 | 800 | 790 | 750 | 800 |
| $SiO_2$ | | 62.2 | 60.4 | 59.4 | 52.3 | | |
| $Al_2O_3$ | | 10.4 | 10.2 | 10.1 | 9.6 | | |
| $B_2O_3$ | | 5.5 | 11.9 | 12.3 | 17.4 | | |
| $TiO_2$ | | 2.2 | — | — | — | | |
| $Li_2O$ | | 1.9 | 1.9 | 1.8 | 1.9 | | |
| $Na_2O$ | | 7.0 | 5.8 | 6.5 | 7.7 | | |
| $K_2O$ | | 6.2 | 5.8 | 6.0 | 5.7 | | |
| CaO | | 4.6 | 4.0 | 3.9 | 2.7 | | |
| BaO | | — | — | — | 2.7 | | |

*25–500° C.

EXAMPLE 4

Another bonding dental ceramic containing an opacifier was prepared as in Example 1 by mixing the following raw materials:

| RAW MATERIAL | SUPPLIER | WEIGHT-PERCENT |
| --- | --- | --- |
| Feldspar | Dentsply International, York, PA | 28.0 |
| Quartz Flour | Bremthaler Quarzwerke, Usingen | 34.0 |
| $Na_2CO_3$ | Emesco, Frankfurt | 5.0 |
| $KNO_3$ | Riedel-de Haen, Seelze (Art. No. 12651) | 6.0 |
| $Li_2CO_3$ | Merck, Darmstadt (Art. No. 5670) | 6.0 |
| $CaCO_3$ | Merck, Darmstadt (Art. No. 2069) | 6.0 |
| $B_2O_3$ | Riedel-de Haen, Seelze (Art. No. 31145) | 7.0 |
| $Na_2B_4O_7 \cdot 10H_2O$ | Brenntag AG, Mühlheim/Ruhr | 6.0 |
| $TiO_2$, RN56 | Kronos Titan GmbH, Leverkusen | 2.0 |

Mixing, fusing, milling in water, drying, and grinding is carried out as in Example 1.

The resulting bonding dental ceramic containing an opacifier had the following composition:

| COMPOUND | WEIGHT-PERCENT |
| --- | --- |
| $SiO_2$ | 61.6 |
| $Al_2O_3$ | 6.4 |
| $K_2O$ | 7.0 |
| $Na_2O$ | 5.6 |
| $Li_2O$ | 2.8 |
| CaO | 3.9 |
| $B_2O_3$ | 10.5 |
| $TiO_2$ | 2.2 |

The bonding dental ceramic was subjected to a firing temperature of 790° C. and had a coefficient of thermal expansion of $8.6 \times 10^{-6}$/K (25°–500° C.). The resultant bond strength was determined to be 22 ±2 MPa according to the Schmitz/Schulmeyer method.

Preferred bonding, opacifying, body and incisal dental ceramic compositions for use in accordance with the invention are shown in Table II.

TABLE II

| | Bonding Dental Ceramic | Opacifying | Body and Incisal |
| --- | --- | --- | --- |
| $SiO_2$ | 63.7 | 51.4 | 64.1 |
| $Al_2O_3$ | 6.5 | 10.0 | 12.3 |
| $K_2O$ | 7.1 | 7.3 | 8.1 |
| $Na_2O$ | 5.7 | 5.0 | 6.1 |
| $Li_2O$ | 2.4 | 1.5 | 1.8 |
| CaO | 3.9 | 2.1 | 2.2 |
| $B_2O_3$ | 10.7 | 3.7 | 5.4 |
| $SnO_2$ | | 19.0 | |

While present embodiments of the invention and methods of practicing the same have been illustrated and described, it will be recognized by those skilled in the art that this invention may be otherwise variously embodied and practiced within the scope of the following claims.

What is claimed is:

1. A fused dental material, comprising: a base and a dental ceramic material, said dental ceramic material comprising from 5 to 12 percent by weight $Al_2O_3$, from 54 to 64 percent by weight $SiO_2$, from 3 to 10 percent by weight of $Na_2O$ and between 8 and 17 percent by weight $B_2O_3$, said dental ceramic material being fused to said base to provide a ceramic coating fused to said base, said base material consisting essentially of titanium wherein said dental ceramic material has a coefficient of thermal expansion of from $7.8 \times 10^{-6}$/K to $9.0 \times 10^{-6}$/K (25°–500° C.) and fuses to said base at temperatures less than 850° C.

2. The fused dental material of claim 1 wherein said base material consists of titanium.

3. The fused dental material of claim 1 wherein said dental ceramic material comprises from 54 to 64 percent by weight $SiO_2$; from 5 to 12 percent by weight $Al_2O_3$, 8 to 17 percent by weight $B_2O_3$ 0.01 to 6 percent by weight $Li_2O$ 3 to 10 percent by weight $Na_2O$, 0.01 to 8 percent by weight $K_2O$, 0.01 to 2 percent by weight MgO, 0.01 to 5 percent by weight CaO, and 0.01 to 2 percent by weight BaO.

4. The fused dental material of claim 1 wherein said dental ceramic material contains less than or equal to 0.5 percent by weight fluoride.

5. The fused dental material of claim 1 wherein said dental ceramic material is bonded to said base with a bond strength of at least 20 MPa determined by the Schmitz/Schulmeyer method by fusing said dental ceramic material to said base at a temperature of less than 830° C., and less than or equal to 5 percent by weight of additive selected from the group consisting of pigment and opacifier.

6. The fused dental material of claim 1 wherein said dental ceramic material is fused to said base at a temperature of less than 830° C., and contains less than or equal to 0.5 percent by weight fluoride.

7. The fused dental material of claim 2 wherein said dental ceramic material is fused to said base at a temperature of less than 830° C., and contains less than or equal to 0.5 percent by weight fluoride.

8. The fused dental material of claim 5 wherein said pigment and opacifier is metal oxide having less than 5% transparency to a broad spectrum of visible light.

9. The fused dental material of claim 1 further comprising an agent which effectively reduces the melting point of said dental ceramic material and wherein said dental ceramic is fused to said base at a temperature less than 800° C.

10. The fused dental material of claim 1 wherein said dental ceramic material is fused to said base at a temperature less than 830° C., and contains less than or equal to 5 percent by weight of one or more additives selected from the group consisting of pigment and opacifier.

11. A dental ceramic material that can be fused to dental prostheses consisting essentially of titanium comprising:

from 54 to 64 percent by weight $SiO_2$, from 5 to 12 percent by weight $Al_2O_3$, 8 to 17 percent by weight $B_2O_3$; 0.1 to 6 percent by weight $Li_2O$, 3 to 10 percent by weight $Na_2O$; 0.1 to 8 percent by weight $K_2O$, 0.1 to 2 percent by weight MgO; 0.1 to 5 percent by weight CaO, and 0.1 to 2 percent by weight BaO; wherein said material has a coefficient of thermal expansion of from $7.8 \times 10^{-6}$/K to $9.0 \times 10^{-6}$/K (25°–500° C.) and can be fused to a base material consisting essentially of titanium at temperatures above 740° C. and less than 850° C.

12. The dental ceramic material of claim 11 wherein said $B_2O_3$ is between 8 to 13 percent by weight of said dental ceramic material and said material is fused at temperatures less than 830° C.

13. The dental ceramic material of claim 11 further comprising polymerizable compounds, opacifiers or pigments and wherein said dental ceramic material is a powder suspension or spreadable paste which is self curable or curable by visible light.

14. The dental ceramic material of claim 12 further comprises organic compounds that are capable of being completely burned out upon firing of said dental ceramic material.

* * * * *